(12) United States Patent
Trieu et al.

(10) Patent No.: US 9,101,400 B2
(45) Date of Patent: Aug. 11, 2015

(54) ROTATIONAL OFFSET OVAL VERTEBRAL ROD

(71) Applicant: Warsaw Orthopedic, Inc., Warsaw, IN (US)

(72) Inventors: Hai H. Trieu, Cordova, TN (US); Christopher M. Patterson, Olive Branch, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 20 days.

(21) Appl. No.: 13/789,262

(22) Filed: Mar. 7, 2013

(65) Prior Publication Data

US 2014/0257393 A1    Sep. 11, 2014

(51) Int. Cl.
*A61B 17/70*    (2006.01)

(52) U.S. Cl.
CPC ........... *A61B 17/7004* (2013.01); *A61B 17/701* (2013.01); *A61B 17/7026* (2013.01)

(58) Field of Classification Search
CPC ............. A61B 17/701; A61B 17/7019; A61B 17/7026
USPC .................................................. 606/254, 255
See application file for complete search history.

(56) References Cited

U.S. PATENT DOCUMENTS

| | | | | |
|---|---|---|---|---|
| 4,743,260 A * | 5/1988 | Burton | .......................... | 128/898 |
| 6,099,528 A * | 8/2000 | Saurat | ........................... | 606/254 |
| 6,966,910 B2 * | 11/2005 | Ritland | ......................... | 606/257 |
| 8,043,339 B2 * | 10/2011 | Hudgins et al. | ................ | 606/255 |
| 2003/0191470 A1 * | 10/2003 | Ritland | ............................ | 606/61 |

FOREIGN PATENT DOCUMENTS

EP    2468201 A1 *   6/2012    ............. A61B 17/70

* cited by examiner

*Primary Examiner* — Pedro Philogene
*Assistant Examiner* — David Comstock (57) ABSTRACT

A flexible connection unit for use in a spinal fixation device is provided. The flexible connection unit includes an elongated member, such as a vertebral rod, having a first end portion and a second end portion opposite each other with a transition portion extending therebetween. The first end portion of the vertebral rod comprises an oval shape and the second end portion contains an oval or non-oval shape. The major diameter of the oval shaped first end is parallel to the sagittal plane of a patient's body and provides the higher stiffness for fusion to resist flexion in the sagittal plane. The second end portion of the vertebral rod is perpendicular to the sagittal end of a patient's body and provides the lower stiffness for fusion.

20 Claims, 5 Drawing Sheets

ROTATIONAL OFFSET OVAL VERTEBRAL ROD

TECHNICAL FIELD

The present disclosure generally relates to medical devices for the treatment of musculoskeletal disorders, and more particularly to a vertebral rod, which provides stability while reducing stress on spinal elements.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, they may fail to relieve the symptoms associated with these disorders. Surgical treatment of these spinal disorders include discectomy, laminectomy, fusion and implantable prosthetics. As part of these surgical treatments, connecting elements such as vertebral rods are often used to provide stability to a treated region. During surgical treatment, one or more rods may be attached to the exterior of two or more vertebral members.

Rods redirect stresses away from a damaged or defective region while healing takes place to restore proper alignment and generally support the vertebral members. In some applications, rods are attached to the vertebral members without the use of implants or spinal fusion. Flexible connecting elements are also known that permit limited spinal motion of a spinal motion segment. Such flexible connecting elements can provide dynamic spinal support. While prior connecting elements have attempted to provide effective spinal stabilization, there remains a need for connecting elements that provide a dynamic stabilizing resistance to forces and permit motion of a spinal column segment(s) in flexion and extension while effectively stabilizing the spinal column segment(s) and the structural integrity of the connecting element.

Therefore, it would be desirable to provide a spinal rod having a transitional surface with variable stiffness that maintains shear strength and is compatible with existing bone screws.

SUMMARY OF THE INVENTION

Accordingly, a dynamic flexible connection unit is provided, having flexion capability, which provides stability while reducing stress on spinal elements. The flexible connection unit or vertebral rod can include a configuration to provide increased strength and stiffness to the rod while maintaining flexibility at selected portions of the rod. It is envisioned that the disclosed system may be employed as a posterior, anterior and/or lateral dynamic stabilization device. In various embodiments, the flexible connection unit provided can be used to stabilize the spine in conditions, such as for example, proximal junctional kyphosis (PJK) as well as other spinal disorders that need stabilization needs. The components of the vertebral rod system are easily manufactured and assembled.

In one particular embodiment, in accordance with the principles of the present disclosure, a flexible connection unit or vertebral rod is provided. The flexible connection unit includes an elongated member, such as a vertebral rod, having two end portions, a first end portion and a second end portion opposite each other with a transition portion extending therebetween. At least one end portion, for example, the first end portion of the vertebral rod comprises an oval shape and the second end portion contains an oval or non-oval shape. The major diameter of the oval shaped end is parallel to the sagittal plane of a patient's body and provides the higher stiffness for fusion to resist flexion/extension or bending in the sagittal plane. The second end portion of the vertebral rod is perpendicular to the sagittal end of a patient's body and provides the lower stiffness for fusion. The transition portion of the elongated member has a median stiffness.

In various embodiments, a flexible connection unit for use in a spinal fixation device is provided. The flexible connection unit comprises an elongated member, for example, a vertebral rod having a first end portion, a second end portion opposite each other and a transition portion extending therebetween, wherein at least one end portion comprises a major diameter that is parallel to the sagittal plane of a patient's body.

In certain embodiments, the at least one oval shaped end portion of the vertebral rod is rotationally offset along the axis formed by the length of the rod to form an offset rotational angle which can vary in a range from about 1 to about 180 degrees. In some embodiments, the offset rotational angle is about 90 degrees. In other embodiments, a vertebral rod can contain several offsets resulting in elongated portion of different stiffness.

In various embodiments, the elongated member can be a straight or curved vertebral rod. In other embodiments, the elongated rod can contain several curvatures.

In alternate embodiments, the second end portion that is not oval shaped can be a circle, triangular, rectangular, square, polygonal, irregular, uniform, non-uniform, variable and/or tapered and the first end portion can be oval, elliptical, oblong, or other shape having a major diameter.

In various embodiments, the elongated member comprises an outer surface having different surface treatments comprising texturing, shot peening, burnishing or grit blasting. In certain embodiments the outer surface further comprises an osteointegrating coating disposed on the outer layer, the osteointegrating coating comprising an osteoconductive coating, an osteoinductive coating or a mixture thereof.

In several embodiments, osteoconductive material comprises at least one of: hydroxyapatite; a biocompatible ceramic; a calcium sulfate; a calcium phosphate; corraline hydroxyapatite; biphasic calcium phosphate; tricalcium phosphate; fluorapatite; mineralized collagen; bioactive glasses; porous metals; bone particles; demineralized bone matrix (DBM); and mixtures thereof. In other embodiments, the osteoinductive material comprising at least one of: bone morphogenetic proteins; demineralized bone matrix; transforming growth factors; osteoblast cells; growth and differentiation factors; insulin-like growth factor 1; platelet-derived growth factor; fibroblast growth factor; and mixtures thereof.

A method for treating a plurality of spine vertebrae regions is also provided. The method comprises selecting an elongated member having a first end portion, a second end portion opposite each other and a transition portion extending therebetween, wherein a first end portion comprises an oval shape and a second end has an oval or non-oval shape; matching appropriate diameters of the elongated member to spine vertebrae regions; attaching the elongated member to appropriate size bone anchor assemblies attached to the spine vertebrae regions.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

The present disclosure will become more readily apparent from the specific description accompanied by the following drawings, in which.

Like reference numerals indicate similar parts throughout the figures. It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION OF THE INVENTION

The exemplary embodiments of the flexible connection unit and methods of use disclosed are discussed in terms of medical devices for the treatment of spinal disorders. In various embodiments, the flexible connection unit can be a vertebral rod which will be discussed in terms of a dynamic vertebral rod having flexion capability. It is envisioned that the vertebral rod and methods of use disclosed provide stability and maintain structural integrity while reducing stress on spinal elements. It is envisioned that the present disclosure may be employed to treat spinal disorders such as, for example, degenerative disc disease, disc herniation, osteoporosis, spondylolisthesis, stenosis, scoliosis and other curvature abnormalities, kyphosis (e.g., PJK), tumor and fractures. It is further envisioned that the present disclosure may be employed with surgical treatments including open surgery and minimally invasive procedures, of such disorders, such as, for example, discectomy, laminectomy, fusion, bone graft and implantable prosthetics. It is contemplated that the present disclosure may be employed with other osteal and bone related applications, including those associated with diagnostics and therapeutics. It is further contemplated that the disclosed vertebral rod system may be employed in a surgical treatment with a patient in a prone or supine position, employing a posterior, lateral or anterior approach. The present disclosure may be employed with procedures for treating the lumbar, cervical, thoracic and pelvic regions of a spinal column.

Moreover, it is contemplated that the flexible connection unit or vertebral rod provided by this disclosure can be especially useful in the treatment and/or prevention of proximal junctional kyphosis (PJK) sometimes found in scoliosis patients postoperatively after undergoing scoliosis surgery. In the art, PJK has been defined as present in a patient wherein the proximal junctional angle is greater than 108 and at least 108 degrees greater than the corresponding preoperative measurement. (M. Yagi et al., "Incidence, risk factors and classification of proximal junctional kyphosis: surgical outcomes review of adult idiopathic scoliosis," Spine, vol. 36(1):E60-8, Jan. 1, 2011). Alternatively, it is contemplated that the connection unit may likewise be employed in highly kyphotic cases such as Scheuermann's kyphosis where the stiffness of the construct would be greatest at the kyphotic region. Thus, in one embodiment, the stiffer part of the flexible connection unit may be caudal to the more flexible part of the connection unit for treating, for example, PJK. In another embodiment, the stiffer portion of the connection unit may be cephalic for increased stiffness in deformity cases such as Scheuermann's kyphosis.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

As used herein, it is understood that the term "coronal plane" includes any plane of section in the anatomical position that generally passes vertically through the human body and is generally perpendicular to both the median (or sagittal) plane and the horizontal (or axial or transverse) plane, generally dividing the human body into anterior and posterior sections, and further includes any plane of section in the anatomical position that generally passes vertically through the human body, is generally perpendicular to the horizontal (or axial or transverse) plane, and is generally angularly oriented from the median (or sagittal) plane at an angle of orientation ranging from greater than zero degrees up to and including ninety degrees.

Furthermore, as used herein, it is understood that the term "sagittal plane" includes any plane of section in the anatomical position that generally passes vertically through the human body in the prone position and is generally perpendicular to both the coronal plane and the horizontal (or axial or transverse) plane, generally dividing the human body into left and right sections, and further includes any plane of section in the anatomical position that generally passes vertically through the human body in the prone position, is generally perpendicular to the horizontal (or axial or transverse) plane, and is generally angularly oriented from the coronal plane at an angle of orientation ranging from greater than zero degrees up to and including ninety degrees.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, portions and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The following discussion includes a description of a flexible connection unit or vertebral rod, related components and exemplary methods of employing the vertebral rod in accordance with the principles of the present disclosure. Alternate embodiments are also disclosed. Reference will now be made in detail to the exemplary embodiments of the present disclosure, which are illustrated in the accompanying figures. Turning now to FIGS. 1-13, there are illustrated components of a flexible connection unit in accordance with the principles of the present disclosure.

The components of the flexible connection unit are fabricated from materials suitable for medical applications, including metals, polymers, ceramics, biocompatible materials and/or their composites, depending on the particular application and/or preference of a medical practitioner. In various embodiments, the flexible connection unit described herein can be a vertebral rod. For example, a vertebral rod, as discussed below, can be fabricated from materials such as commercially pure titanium, titanium alloys, super-elastic titanium alloys, cobalt-chrome alloys, stainless steel alloys, thermoplastics such as polyaryletherketone (PAEK) including polyetheretherketone (PEEK), polyetherketoneketone (PEKK) and polyetherketone (PEK), carbon fiber reinforced PEEK composites, PEEK-BaSO$_4$ composites, biocompatible materials such as polymers including plastics, metals, ceramics and composites thereof, rigid polymers including polyphenylene, polyamide, polyimide, polyetherimide, polyethylene, polyurethane, epoxy, silicone; and different sections of the rod may have alternative material composites to achieve various desired characteristics such as strength, rigidity, elasticity, compliance biomechanical performance, durability and radiolucency or imaging preference. In various embodiments, the flexible connection unit can be fabricated from materials comprising cobalt chromium alloys, titanium, titanium alloy, nitinol, stainless steel, PEEK, carbon reinforced PEEK or a mixture thereof.

In some embodiments, the vertebral rod can be formed of two or more materials. In one embodiment, elongated rod sections can be fabricated from carbon-reinforced PEEK and an intermediate section can be fabricated from PEEK. In another embodiment, elongated rod sections are fabricated from PEEK and an intermediate section is fabricated from carbon-reinforced PEEK. It is envisioned that the rod or device can be manufactured via various methods including machining, casting, injection-molding, insert-molding, overmolding, compression molding, transfer molding, co-extrusion, pultrusion, dip-coating, spray-coating, powder-coating, porous-coating, and their combinations. One skilled in the art, however, will realize that such materials and fabrication methods suitable for assembly and manufacture, in accordance with the present disclosure, would be appropriate.

With reference to FIGS. 1-5, flexible connection unit 10 is configured for attachment to vertebrae during surgical treatment of a spinal disorder, examples of which are discussed herein. In various embodiments, flexible connection unit 10 has an elongated member 20 having a first end portion 22, a second end portion 24 opposite first end portion 22 and an intermediate portion 26 disposed therebetween as joining the first end portion 22 to the second end portion 24. A longitudinal axis, A1 is defined between first end portion 22, along intermediate portion 26 to second end portion 24.

Figure 1:
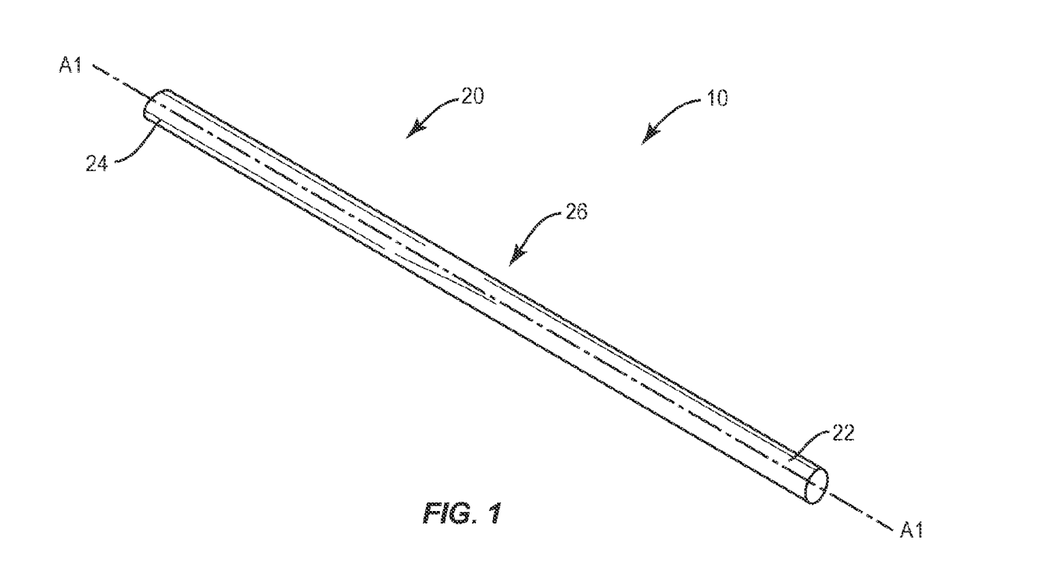
FIG. 1 is a perspective view of one particular embodiment of a straight flexible connection unit in accordance with the principles of the present disclosure.
Figure 2:
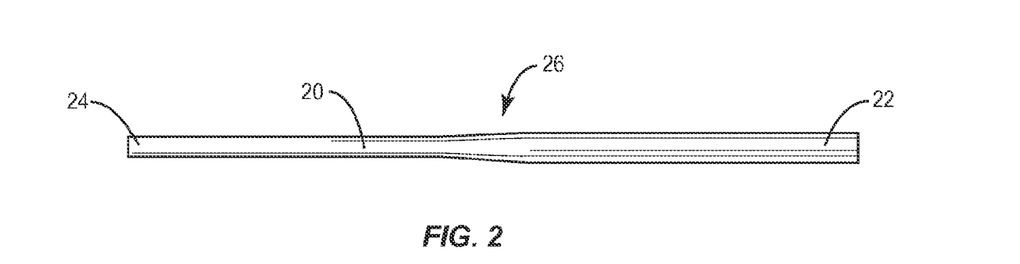
FIG. 2 is a side view of the flexible connection unit shown in FIG. 1.
Figure 3:
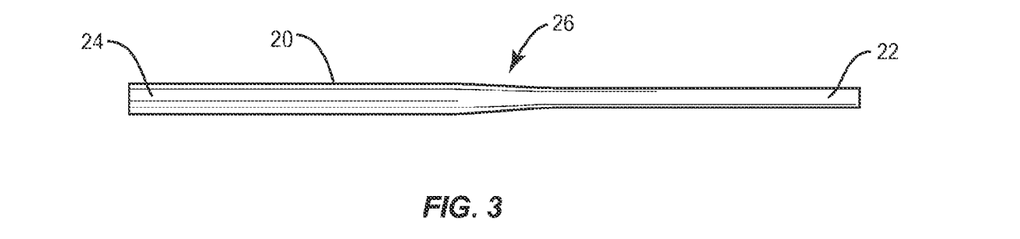
FIG. 3 is a top view of the flexible connection unit shown in FIG. 1.
Figure 4:
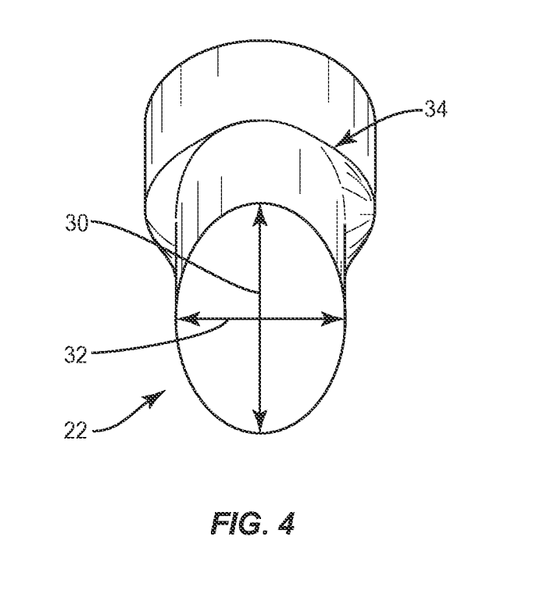
FIG. 4 is a perspective end view of a first end portion of the flexible connection unit shown in FIG. 1.

First end portion 22 can have a generally cylindrical geometry, however other shapes are possible, for example, oval, elliptical, and/or oblong as long as it has a major diameter. In various embodiments, as illustrated in FIG. 4, first end portion 22 has an oval shape, wherein the cross-section has its major diameter 30 parallel to the sagittal plane. First end 22 also contains a minor diameter 32 extending transverse to major diameter 30.

Major diameter 30 of the at least one oval shaped first end portion 22 can have many dimensions depending upon the intended surgical application.

Figure 5:
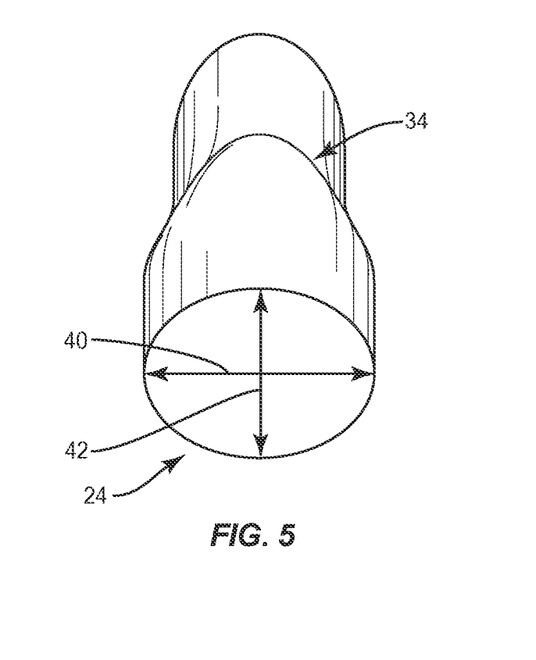
FIG. 5 is a perspective end view of a second end portion of the flexible connection unit shown in FIG. 1.
Figure 6:
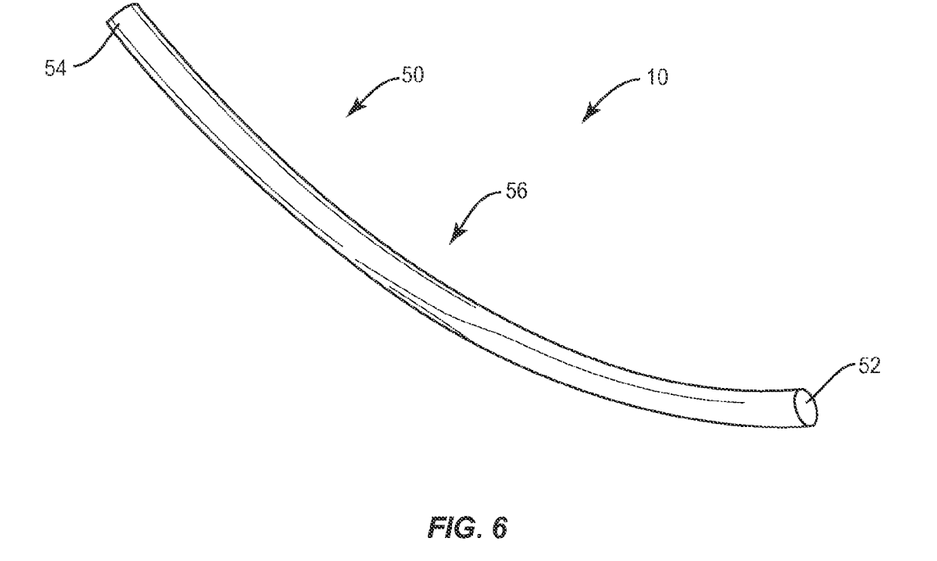
FIG. 6 is a perspective view of another particular embodiment of a curved flexible connection unit in accordance with the principles of the present disclosure.
Figure 7:
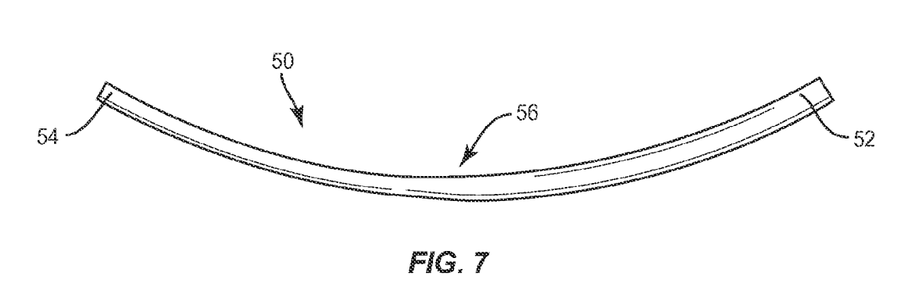
FIG. 7 is a side view of the flexible connection unit shown in FIG. 6.
Figure 8:
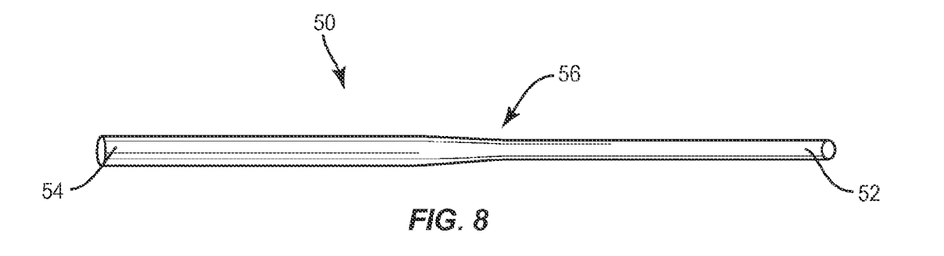
FIG. 8 is a top view of the flexible connection unit shown in FIG. 6
Figure 9:
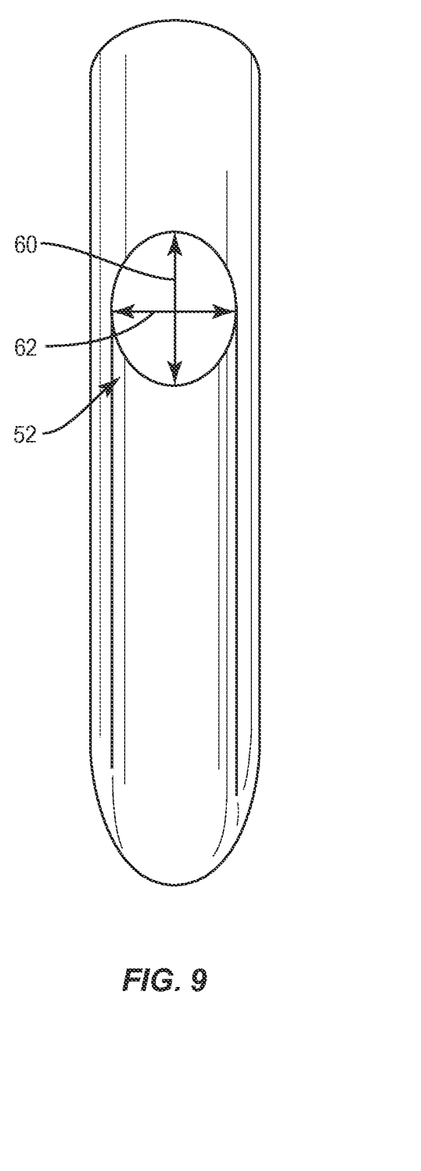
FIG. 9 is a perspective end view of a first end portion of the flexible connection unit shown in FIG. 6.
Figure 10:
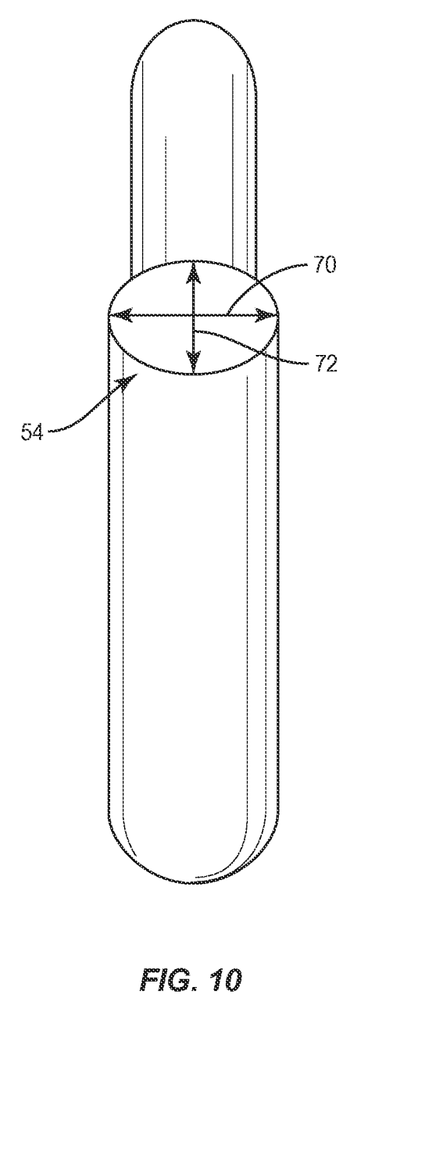
FIG. 10 is a perspective end view of a second end portion of the flexible connection unit shown in FIG. 6.

Second end portion 24 can have a generally cylindrical geometry however other shapes are possible, for example, oval, elliptical, oblong, triangular, rectangular, square, polygonal, irregular, uniform, non-uniform, variable and/or tapered. In various embodiments, as illustrated in FIG. 5, second end portion 24 has an oval shape, wherein the cross-section has its major diameter 40 perpendicular to the sagittal plane. The cross section of second end portion 24 also contains a minor diameter 42 extending transverse to major diameter 40. Minor diameter 42 of second end portion 24 is smaller than major diameter 30 of first end portion 22. As shown in FIGS. 4-5, first and second end portions 22, 24 are offset such that minor diameter 42 is in substantially coaxial alignment with major diameter 30.

Major diameter 40 of second end portion 24 can have many dimensions depending upon the intended surgical application. In some embodiments, it is contemplated that major diameter 30 of the first end portion 22 is larger in size than major diameter 40 of second end 24. It is envisioned that the ratio of major diameter 30 of the first end portion 22 to major diameter 40 of the second end portion 24 varies from about 1.01 to about 2.

It will be understood that a first end of the rod comprises an oval shape and the second end of the rod comprises an oval or non-oval shape. The oval shaped first end can be positioned parallel or substantially parallel to the sagittal plain for fusion and the oval or non-oval shaped second end can be positioned perpendicular or substantially perpendicular to the sagittal plane. The oval or non-oval shaped second end will be less stiff than the oval shaped first end by at least 1%, 5%, 10% or 15% when the rod is in this position. The difference in stiffness between first and second end portions 22, 24 in the sagittal plane increases with an increase in the offset between major diameters 30, 40 of first and second portions 22, 24, respectively, until the difference in stiffness is maximized at an offset of 90 degrees. The difference in stiffness between first and second end portions 22, 24 can be increased by increasing the perimeter of a cross section of first end portion 22 relative to second end portion 24, and/or by reducing the perimeter of a cross section of second end portion 24 relative to first end portion 22. The difference in the stiffness between first and second end portions 22, 24 can also be increased by changing the materials of the first and second end portions 22, 24 and/or by increasing the ratio between the size of major diameter 30 of first end portion 22 and the size of minor diameter 42 of second end portion 24. In some embodiments, the rod has a flexural rigidity from about 0.1 N-m² to about 75 N-m² or from about 0.5 N-m² to about 50 N-m², with the first end and/or second end having, in some embodiments, differing flexural rigidity relative to each other. In one embodiment, the first and second ends are variously shaped, such as, for example, circular, rectangular, polygonal, irregular, tapered, offset, staggered, uniform and non-uniform.

In some embodiments, elongated member 20 can be a straight rod as illustrated in FIGS. 1-5 or a curved rod as illustrated in FIGS. 6-13. In the embodiments illustrated in FIGS. 6-13, flexible connection units 10 contain one curvature, however, multiple curvatures are contemplated.

Commonly, spinal rods are cylindrical, and have one consistent cross-section throughout their lengths. Absent a variation in materials within a rod, the size of the cross-section determines the strength of the rod.

The spine, however, consists of a stack of 33 curved vertebrae that are structurally divided into five regions, namely, cervical region (C1-C7), thoracic region (T1-T12), lumbar region (L1-L5) and, finally, the fused sacrum and coccyx regions. Lower down the spine, the vertebrae become larger as the spine supports heavier loads. The cervical vertebrae, forming the neck areas, are relatively small. Just below the cervical vertebrae are the thoracic vertebrae, which form the upper back. The thoracic vertebrae are larger than the cervical vertebrae, and increase in size from top to bottom. Below the thoracic region lies the lumbar vertebrae, which are even larger and support the weight of the entire upper body. Relative motion in the spine may also vary along the length of the spinal column, as the cervical vertebra have a greater range of motion than the lower lumbar vertebra. The elongated member may transition similar to the natural structure of the spine, with the more flexible portion of the rod oriented higher along the spinal column.

In various embodiments, it is therefore desirable for a flexible connection unit such as, for example, elongated member or vertebral rod 20 to exhibit variable stiffness along its length depending upon its location along the spine. Accordingly, as shown in FIGS. 1-5 for a straight vertebral rod 20 and FIGS. 6-10 for a curved vertebral rod 50 a 90 degree rotational offset of the major diameter 30 of the first end portion 22 along the length of elongated member 20 to reach major diameter 40 of second end portion 24 may be used to maximize the difference in stiffness between first end portion 22 and second end portion 24 of elongate member 20.

While some embodiments may include increasing stiffness as the rod transitions caudally from cervical through thoracic and lumbar regions, another embodiment may make the elongated member more flexible above a region having a more flexible elongated member. In such an embodiment the stiffer section of the rod may be nearer a region where a deformity creates a need for aggressive correction, thus placing higher loads on the elongated member. At the first end portion 22, where major diameter 30 is parallel or substantially parallel to the sagittal plane, elongated member 20 experiences the higher stiffness level for spinal fusion. With further reference to FIG. 4, the 90 degree rotational offset of major diameter 30 occurs at an inflexion junction 34. By contrast, at the second end portion 24, where major diameter 40 is perpendicular to the sagittal plane, the level of stiffness is lower, which is especially useful for a transitional level.

With further reference to FIGS. 4 and 5, the 90 degree rotational offset of major diameter 30 occurs at an inflexion junction 34. While FIGS. 2-5 illustrate one rotational offset, a vertebral rod can have multiple offsets differing in their degree of stiffness. The intermediate portion 26 is considered to be a neutral zone having a median level of stiffness to fusion.

As a result, when an elongate section of the vertebral rod is positioned such that its major diameter is substantially parallel with the sagittal plane of the patient, a higher stiffness for fusion can be achieved. At a 90 degree rotational offset, the other elongate section of the rod will have its major diameter substantially perpendicular to the sagittal plane of the patient, which will exhibit lower stiffness for transitioning or topping-off purposes. In various embodiments, the rod may have multiple offsets or elongate sections or various degrees of stiffness.

In other embodiments, as illustrated in FIGS. 6-10, curved elongated member or vertebral rod 50 comprises a first end portion 52 and a second end portion 54 with an intermediate portion 56 disposed therebetween. First end portion 52 has an oval or elliptical cross-section defining major diameter 60 which is parallel to the sagittal plane of a patient's body forming a portion of higher level of stiffness for fusion. Minor diameter 62 is transverse to major diameter 60. Second end 54 also comprises an oval or elliptical cross-section defining a major diameter 70 which is perpendicular to the sagittal plane of a patient's body, forming a portion having a lower level of stiffness. Minor diameter 72 is transverse to major diameter 70. Intermediate portion 56 has a level of stiffness intermediate between that of the first end portion 52 and second end portion 54. As in FIGS. 1-5, in FIGS. 6-10, the first end portion 52 is at 90 degree rotationally offset from the second end portion 54.

Although FIGS. 1-10 illustrate 90 degree rotational offsets of major diameter along the length of the elongated member, rotational offset angles in the range between 1 to 180 degrees are also contemplated.

In certain embodiments, multiple offset angles are contemplated along elongated member 20 from the first end portion 22 to the second portion 24 with reference to a straight rod. In other embodiments, multiple offset angles are contemplated along elongated member 50 from the first end portion 52 to the second portion 54 with reference to a curved rod. Similarly, the cross-sectional area along the rod may be variable. In some embodiments, major diameter 40 of second end 24 is reduced in size by comparison to major diameter 30 of the first end 22.

In various embodiments, the cross section of elongated member can be continuously reduced from the oval shaped first end portion to an oval or non-oval shaped second end portion. In other embodiments, as illustrated in FIGS. 11 and 12, the cross section of the first end portion 82 of elongated member 80 can be round, however, because the major diameter 90, albeit equal to the minor diameter, is substantially parallel with the sagittal plane of the patient, the first end portion 82 can still achieve the higher stiffness for fusion.

Figure 11:
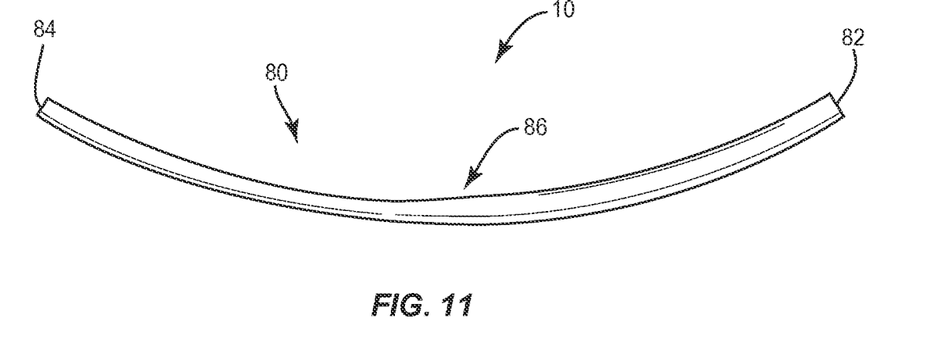
FIG. 11 is a side view of the flexible connection unit of an alternate embodiment of the flexible connection unit in accordance with the principles of the present disclosure.
Figure 12:
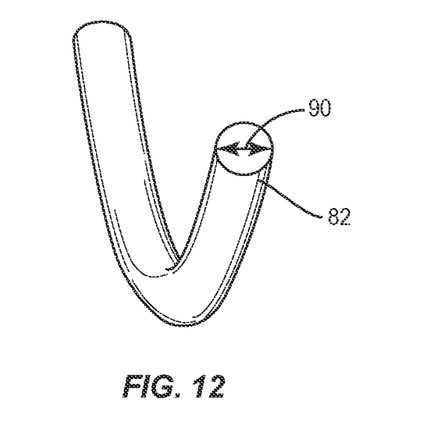
FIG. 12 is a perspective view of the first end portion of the flexible connection unit of FIG. 11.
Figure 13:
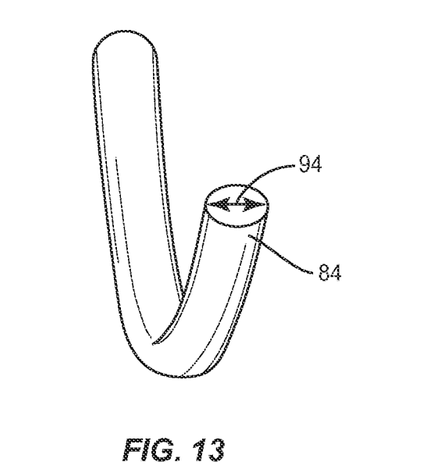
FIG. 13 is a perspective view of the second end portion of the flexible connection unit of FIG. 11.

By contrast, as illustrated in FIGS. 11 and 13, the cross-section of second end portion 84 of elongated member 80 is oval or elliptical. However since the major diameter 94 of the second end portion 84 is perpendicular to the sagittal plane, second end portion 84 is less stiff than first end portion 82 by at least 15%. Intermediate portion 86 of vertebral rod 80 has a level of stiffness intermediate between that of the first end portion 82 and second end portion 84.

The flexible connection unit described herein can be used with various bone screws, pedicle screws or multi-axial screws (MAS) used in spinal surgery. In embodiments where the rod transitions from an oval to a circular cross section, the length of the major axis of the oval portion may be approximately the same as the length of the diameter of the circular section. Such an embodiment may allow the same MAS screws, as well as the same set screws to lock the MAS screws to be used along the entire length of the rod. It is contemplated that the flexible connection unit may be used with pedicle screws coated with an osteoconductive material such as hydroxyapatite and/or osteoinductive agent such as a bone morphogenic protein for enhanced bony fixation to facilitate motion of the treated spinal area. Flexible connection unit 10 can be made of radiolucent materials such as polymers. Radiomarkers may be included for identification under x-ray, fluoroscopy, CT or other imaging techniques. Metallic or ceramic radiomarkers, such as tantalum beads, tantalum pins, titanium pins, titanium endcaps and platinum wires can be used, such as being disposed at the end portions of elongated member 20 and/or along the length thereof.

In various embodiments, the rod can have markers, and or colors that allow the surgeon to easily identify the oval shaped first end and the oval or non-oval shaped second end for ease of implanting the rod into the body.

In various embodiments, the elongated members 20, 50 or 80 comprise an outer surface (not shown) that may have different surface treatments, such as textured, shot-peened, burnished, porous, patterned or wavy. In other embodiments the treated surface can further comprise a coating. The outer surface may be chemically treated or modified using various processes or materials which include oxidation, anodization, plasma treatment, vapor deposition, plating, coating or etching. It is contemplated that the vertebral rod may employ a heterogeneous composite having non-uniform carbon content.

In order to increase the estimated useful life of the elongated member, the outer surface may be treated to maintain fatigue resistance properties. For example, the outer surface can be work hardened by shot peening, followed by coating with an osteointegrating material as more specifically described in U.S. Ser. No. 11/684,467 incorporated herein by reference as if set forth in full.

In some embodiments, the outer layer of elongated members 20, 50 or 80 (not shown) comprises a roughened surface and an osteintegrating coating disposed on the roughened surface. The surface texturing on the outer layer of the elongated member may improve the adhesion of the coating onto the surface of the elongated member. The coating not only increases osteointegration of the elongated member implant but also the resistance to fatigue.

In some embodiments the osteointegrating coating may be either osteoconductive or osteoinductive, or both. The osteointegrating material in the coating may be heterogeneous in some examples and homogeneous in others For example, in addition to, or in place of using HA (hydroxyapatite) as an osteoconductive coating, other exemplary osteoconductive coatings may comprise one or more of: biocompatible ceramics; calcium sulfate; a calcium phosphate such as HA, corraline hydroxyapatite, biphasic calcium phosphate, tricalcium phosphate, or fluorapatite; mineralized collagen; bioactive glasses; porous metals; bone particles; and demineralized bone matrix (DBM).

An osteoinductive coating may include: other forms of bone morphogenetic proteins (BMP), such as BMP-2, BMP-4, BMP-7, rhBMP-2, or rhBMP-7; demineralized bone matrix (DBM); transforming growth factors (TGF, e.g., TGF-β); osteoblast cells; growth and differentiation factor (GDF); insulin-like growth factor 1, platelet-derived growth factor, fibroblast growth factor, or any combination thereof.

In a further example, an osteoinductive coating material may include HMG-CoA reductase inhibitors, such as a member of the statin family, such as lovastatin, simvastatin, pravastatin, fluvastatin, atorvastatin, cerivastatin, mevastatin, pharmaceutically acceptable salts esters or lactones thereof, or any combination thereof. With regard to lovastatin, the substance can be either the acid form or the lactone form or a combination of both.

In yet another example, an osteoinductive material may comprise LIM mineralized proteins (LMP), osteoinductive peptides, pharmaceutical agents such as antibiotics, pain medication, anti-inflammatory drugs, steroids, osteogenic compositions such as, therapeutic or infection resistant agent, or one or more of the previous in combination.

In some embodiments, the osteointegrating coating material may include multifunctional polymeric materials that inhibit adhesion and immune recognition between cells and tissue. These materials may include a tissue-binding component and a tissue non-binding component. Specific materials may include PEG/PLL copolymers with molecular weights greater than 300, with structures that include AB copolymers, ABA copolymers, and brush-type copolymers.

Additionally, the osteointegrating coating may use grafted polyionic copolymers that are able to attach to biological and non-biological samples to control cell-surface, cell-cell, and tissue-surface interactions. The coating may also include the application of polyionic, PEG-grafted copolymers.

In one embodiment, the osteointegrating coating contains grafted non-interactive material such as PEG (polyethylene glycol) or PEO (polyethylene oxide) within the polymer. Another example coating may be a combination wherein the polymer is a PEG-grafted poly(amino acid) with a polycationic backbone made of lysine, histidine, arginine or ornithine in D-, L-, or DL-configuration, or the polymer is a PEG-grafted polymer with a cationic backbone of a polysaccharide such as chitosan, partially deacetylated chitin, and amine-containing derivatives of neutral polysaccharides, or the polymer is a PEG-grafted non-peptide polyamine with a polycationic backbone such as poly(aminostyrene), poly (aminoacrylate), poly(N-methyl aminoacrylate), poly(N-ethylaminoacrylate), poly(N,N-dimethyl aminoacrylate), poly(N,N-diethylaminoacrylate), poly(aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), polymers of quaternary amines, such as poly(N,N, N-trimethylaminoacrylate chloride), poly(methacrylamidopropyltrimethyl ammonium chloride), or the polymer is a PEG-grafted charged synthetic polymer with a polycationic backbone such as polyethyleneimine, polyamino(meth)acrylate, polyaminostyrene, polyaminoethylene, poly(aminoethyl)ethylene, polyaminoethylstyrene, and N-alkyl derivatives thereof.

Other embodiments include one more coatings comprising a copolymer, wherein the copolymer is a PEG-grafted copolymer with an anionic backbone of a poly(amino acid) grafted with poly(ethylene glycol) where the amino acid contains an additional pendant carboxy group imparting a negative charge to the backbone at pH above 4 and in particular at neutral pH such as polyaspartic acid or polyglutamic acid; or a natural or unnatural polymer with pendant negatively charged groups, particularly carboxylate groups, including alginate, carrageenan, furcellaran, pectin, xanthan, hyaluronic acid, heparin, heparan sulfate, chondroitin sulfate, dermatan sulfate, dextran sulfate, poly(meth)acrylic acid, oxidized cellulose, carboxymethyl cellulose and crosmarmelose, synthetic polymers and copolymers containing pendant carboxyl groups, such as those containing maleic acid or fumaric acid in the backbone.

In yet another embodiment, the osteointegrating coating comprises nanoparticles, wherein each particle is generally less than 500 nm in diameter. The nanoparticles act to reduce protein "denaturation" as well as subsequent foreign body reactions. Nanoparticles may include a metal particle, carbon particle, inorganic chemical particle, organic chemical particle, ceramic particle, graphite particle, polymer particle, protein particle, peptide particle, DNA particle, RNA particle, bacteria/virus particle, hydrogel particle, liquid particle or porous particle. Thus, the nanoparticles may be, for example, metal, carbon, graphite, polymer, protein, peptide, DNA/RNA, microorganisms (bacteria and viruses) and polyelectrolyte. Polymers may include copolymers of water soluble polymers, including, but not limited to, dextran, derivatives of poly-methacrylamide, PEG, maleic acid, malic acid, and maleic acid anhydride and may include these polymers and a suitable coupling agent, including 1-ethyl-3(3-dimethylaminopropyl)-carbodiimide, also referred to as carbodiimide. Polymers may be degradable or nondegradable or of a polyelectrolyte material. Degradable polymer materials include poly-L-glycolic acid (PLGA), poly-DL-glycolic, poly-L-lactic acid (PLLA), PLLA-PLGA copolymers, poly (DL-lactide)-block-methoxy polyethylene glycol, polycaprolacton, poly(caprolacton)-block-methoxy polyethylene glycol (PCL-MePeg), poly(DL-lactide-co-caprolactone)-block-methoxy polyethylene glycol (PDLLACL-MePEG), some polysaccharide (e.g., hyaluronic acid, polyglycan, chitoson), proteins (e.g., fibrinogen, albumin, collagen, extracellular matrix), peptides (e.g., RGD, polyhistidine), nucleic acids (e.g., RNA, DNA, single or double stranded), viruses, bacteria, cells and cell fragments, organic or carbon-containing materials, as examples. Nondegradable materials include natural or synthetic polymeric materials (e.g., polystyrene, polypropylene, polyethylene teraphthalate, polyether urethane, polyvinyl chloride, silica, polydimethyl siloxane, acrylates, arcylamides, poly(vinylpyridine), polyacroleine, polyglutaraldehyde), some polysaccharides (e.g., hydroxypropyl cellulose, cellulose derivatives, DEXTRAN, dextrose, sucrose, FICOLL, PERCOLL, arabinogalactan, starch), and hydrogels (e.g., polyethylene glycol, ethylene vinyl acetate, N-isopropylacrylamide, polyamine, polyethyleneimine, poly-aluminum chloride).

Movement of the components of the vertebral rod between one and a plurality of orientations is contemplated and may include a range of increasing and decreasing levels of resistance of the components of the vertebral rod.

In assembly, operation and use, the vertebral flexible rod is employed with a surgical procedure for treatment of a spinal disorder affecting a section of a spine of a patient, as discussed herein. The vertebral rod may also be employed with other surgical procedures. In particular, the vertebral rod is employed with a surgical procedure for treatment of a condition or injury of an affected section of the spine to provide stability for healing and therapeutic treatment, while allowing a desirable range of motion or load-sharing capability.

In use, to treat the affected section of the spine, a medical practitioner obtains access to a surgical site including vertebra V in any appropriate manner, such as through incision and retraction of tissues. It is envisioned that the vertebral rod may be used in any existing surgical method or technique including open surgery, mini-open surgery, minimally invasive surgery and percutaneous surgical implantation, whereby the vertebrae V is accessed through a mini-incision, or sleeve that provides a protected passageway to the area. Once access to the surgical site is obtained, the particular surgical procedure is performed for treating the spinal disorder. The vertebral rod is then employed to augment the surgical treatment. The vertebral rod can be delivered or implanted as a pre-assembled device or can be assembled in situ. The vertebral rod may be completely or partially revised, removed or replaced.

In some embodiments, there is a method for treating a plurality of vertebrae regions in a patient in need of such treatment, the method comprising: attaching to the vertebrae regions an elongated member having a first end portion, a second end portion opposite the first end portion and a transition portion extending therebetween, wherein the first end portion comprises an oval shape having a major diameter and the second end portion comprises an oval or non-oval shape; the major diameter of the oval shape of the first end portion configured to be positioned substantially parallel to the sagittal plane of a patient's body.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A flexible connection unit for use in a spinal fixation device comprising an elongated member having a first end portion, a second end portion opposite the first end portion and a transition portion extending therebetween, wherein the first end portion comprises an oval shape having a major diameter and the second end portion comprises an oval or non-oval shape, the major diameter of the oval shape of the first end portion configured to be positioned substantially parallel to a sagittal plane of a patient's body, wherein the major diameter of the first end portion is rotationally offset from a major diameter of the second end portion between 1 and 180 degrees when the elongated member is in an unstressed state.

2. A flexible connection unit of claim 1, wherein the elongated member comprises a vertebral rod.

3. A flexible connection unit of claim 2, wherein the second end portion comprises an oval shape.

4. A flexible connection unit of claim 2, wherein (i) the first end portion is offset from the second end portion by about 90 degrees of rotation in an axial plane of the rod; (ii) the rod has a stiffness dependent upon a rotational offset between the first end portion and the second end portion; (iii) a relative stiffness difference of the rod between the first and second end portions can be increased by increasing a cross section of a stiffer section of the rod or decreasing the cross section of a less stiff section of the rod; or (iv) a relative stiffness difference of the rod between the first and second end portions can be increased by increasing a ratio of the major diameter to minor diameter of the first end portion and/or second end portion of the rod.

5. A flexible connection unit of claim 2, wherein the major diameter of the oval shaped first end portion is rotationally offset from the major diameter of the second end portion about 90 degrees.

6. A flexible connection unit of claim 2, wherein the rod comprises multiple offset angles from the first end portion to the second end portion.

7. A flexible connection unit of claim 2, wherein the elongated member comprises a cross-section that is asymmetrically varied from the oval shaped first end portion to the oval or non-oval shaped second end portion.

8. A flexible connection unit of claim 2, wherein the rod material comprises cobalt chromium alloys, titanium, titanium alloy, nitinol, stainless steel, PEEK, carbon reinforced PEEK or a mixture thereof.

9. A flexible connection unit of claim 1, wherein the second end portion has a lower stiffness than the first end portion by at least 1% in the sagittal plane.

10. A flexible connection unit of claim 9, wherein the second end portion is located caudally relative to the first end portion.

11. A flexible connection unit of claim 1, wherein the second end portion has a lower stiffness than the first end portion by at least 5% in the sagittal plane.

12. A flexible connection unit of claim 1, wherein the transition portion of the elongated member has a higher stiffness than the second end portion and a lower stiffness than the first end portion for spinal fusion.

13. A flexible connection unit of claim 1, wherein the major diameter of the second end portion is less than the major diameter of the first end portion and a major diameter of the transition portion.

14. A flexible connection unit of claim 1, wherein the elongated member comprises a straight rod.

15. A flexible connection unit of claim 1, wherein the elongated member comprises a curved rod.

16. A flexible connection unit of claim 1, wherein the elongated member has a flexibility of from about 0.1 N-m$^2$ to about 75 N-m$^2$ or from about 0.5 N-m$^2$ to about 50 N-m$^2$.

17. A flexible connection unit of claim 1, wherein the elongated member comprises an outer surface treated by texturing, shot peening, burnishing or grit blasting.

18. A flexible connection unit of claim 17, wherein the outer surface comprises an osteoconductive coating, an osteoinductive coating or a mixture thereof.

19. A method for treating a plurality of vertebrae regions in a patient in need of such treatment, the method comprising:
attaching to the vertebrae regions the flexible connection unit recited in claim 1 such that the major diameter of the first end portion is substantially parallel to the sagittal plane of the patient's body.

20. A method according to claim 19, wherein the elongated member comprises a vertebral rod.

* * * * *